United States Patent [19]
Brown

[11] Patent Number: 5,888,984
[45] Date of Patent: Mar. 30, 1999

[54] PHARMACEUTICAL COMPOSITION OF COMPLEX CARBOHYDRATES AND ESSENTIAL OILS AND METHODS OF USING THE SAME

[75] Inventor: Harold G. Brown, Parkville, Mo.

[73] Assignee: Dermal Research Laboratories, Inc., Parkville, Mo.

[21] Appl. No.: 241,692

[22] Filed: May 12, 1994

[51] Int. Cl.$^6$ .................. A61K 31/715; A61K 31/70; A61K 31/725; A61K 35/78

[52] U.S. Cl. ............... 514/54; 424/195.1; 424/DIG. 13; 514/53; 514/55; 514/56; 514/61; 514/62; 514/885; 514/886

[58] Field of Search .................. 424/195.1, DIG. 13, 424/449; 514/54, 56, 62, 63, 825, 828, 829, 830, 848, 862, 863, 866, 886, 887, 906, 907, 921, 925, 928, 929, 930, 946, 947, 969, 885

[56] References Cited

U.S. PATENT DOCUMENTS

| | | | |
|---|---|---|---|
| 4,141,973 | 2/1979 | Balazs | 514/54 |
| 4,148,893 | 4/1979 | Smith | 424/195.1 |
| 4,353,896 | 10/1982 | Levy | 424/195.1 |
| 4,440,777 | 4/1984 | Zupan | 424/195.1 |
| 4,463,016 | 7/1984 | Burgess | 514/947 |
| 4,521,411 | 6/1985 | Koloff | 424/195.1 |
| 4,564,521 | 1/1986 | Altadonna | 514/947 |
| 4,708,873 | 11/1987 | Schulte | 424/195.1 |
| 4,782,046 | 11/1988 | Brown et al. | 514/54 |
| 4,797,402 | 1/1989 | Dorsey | 514/171 |
| 4,800,197 | 1/1989 | Kowcz et al. | 514/162 |
| 4,808,576 | 2/1989 | Schultz et al. | 514/54 |
| 4,847,078 | 7/1989 | Sheppard et al. | 514/777 |
| 4,883,664 | 11/1989 | Sharkey | 424/195.1 |
| 4,895,727 | 1/1990 | Allen | 514/947 |
| 4,900,550 | 2/1990 | Lowry | 424/195.1 |
| 4,917,890 | 4/1990 | McAnalley | 424/195.1 |
| 4,933,184 | 6/1990 | Tsuk | 424/449 |
| 5,009,890 | 4/1991 | Dipippo | 424/195.1 |
| 5,028,429 | 7/1991 | Gochenouer | 424/195.1 |
| 5,082,656 | 1/1992 | Hui et al. | 514/772.6 |
| 5,096,709 | 3/1992 | VanderSloot | 424/195.1 |
| 5,106,622 | 4/1992 | Sherwood et al. | 424/195.1 |
| 5,166,331 | 11/1992 | della Valle et al. | 514/54 |
| 5,179,086 | 1/1993 | Flender | 514/863 |
| 5,215,759 | 6/1993 | Mausner | 424/489 |
| 5,223,257 | 6/1993 | Arora | 424/195.1 |
| 5,266,318 | 11/1993 | Taylor-McCord | 424/195.1 |
| 5,308,838 | 5/1994 | McAnalley et al. | 514/54 |
| 5,331,012 | 7/1994 | Riddick et al. | 514/692 |
| 5,350,774 | 9/1994 | Palou | 514/944 |
| 5,362,497 | 11/1994 | Yamada et al. | 424/449 |
| 5,460,821 | 10/1995 | Masiz | 424/449 |
| 5,559,103 | 9/1996 | Gaeta et al. | 514/54 |
| 5,604,200 | 2/1997 | Taylor-McCord | 514/8 |

FOREIGN PATENT DOCUMENTS

| | | |
|---|---|---|
| 0 444 492 B1 | 9/1991 | European Pat. Off. . |
| 2674749 | 10/1992 | France . |
| 01186824 | 7/1989 | Japan . |
| 9309766 | 5/1993 | WIPO . |
| 9531177 | 11/1995 | WIPO . |

OTHER PUBLICATIONS

The Merck Index—11$^{th}$ Edition, pp. 735, 1072–1078, (1989).
Santus et al., *J. Controlled Release*, vol. 25:1–20, (1993).
Nelson et al., *Blood*, vol. 82(11), pp. 3253–3258, (1992). abstract only.
Foxhall et al., *The Journal of Cell Biology*, vol. 117(4):895–902, (1992).
Tyrrell et al., *Proc. Natl. Acad. Sci., USA*, vol. 88:10372–10376, (1991).
Corbett, *Spec. Chem.*, vol. 11(7):493–4, 496, 501–502, (1991).
Akira Yagi et al., Structure Determination of . . . , Journal of Pharmaceutical Sciences, vol. 73, pp. 62–65, No. 1, Jan. 1984.
David Tyrrell et al., Structural requirements for the . . . , Proc. Natl. Acad. Sci, USA, vol. 88, pp. 10372–10376, Nov. 1991.
Eric L. Radin et al., A Consolidated Concept of . . . , The Journal of Bone and and Joint Surgery, vol. 54–A, pp. 607–616, Apr. 1972.
R.D. Howard et al., Sodium Hyaluronate . . . , The Compendium, vol. 15, No. 3, pp. 473–479, Mar. 1993.
Brian M. Lawrence et al., Progress in Essential Oils, Perfumer & Flavorist, vol. 17, pp. 51–60, Nov./Dec.1992.
A.E. Elkhouly et al., Combined Antibacterial Activity . . . , Australian Journal of Pharmaceutical Sciences, vol. 9, pp. 81–84, Sep. 1980.
Y.K.E. Ibrahim, Aromatic Waters . . . , Pharm. Acta Helv., 66, pp. 286–288, 1991.
A.C. Willians et al., Essential oils as novel human skin . . . , International Journal of Pharmaceutics, vol. 57, R7–R9, 1989.
David H. Adams et al., Leucocyte–endothelial . . . , The Lancet, vol. 343, pp. 831–836, Apr., 1994.
Yoji Shimizu et al., Dual Role of the CD44 Molecule . . . , Journal of Immunology, vol. 143, pp. 2457–2463, No. 8, Oct. 1989.
Michael Munro et al., Expression of Sialyl–Lewis X . . . , American Journal of Pathology, vol. 141, No. 6, pp. 1397–1408, Dec. 1992.

(List continued on next page.)

*Primary Examiner*—Howard C. Lee
*Attorney, Agent, or Firm*—Birch, Stewart, Kolasch & Birch, LLP

[57] ABSTRACT

The invention discloses the discovery that a pharmaceutical composition containing complex carbohydrates and natural or synthetic essential oils can work effectively as a topical pharmaceutical composition. Such pharmaceutical compositions reduce inflammation, assist in wound healing, protect against bruising, relieve itching, relieve pain and swelling and treat topical bacterial infections such as acne and decubitus ulcers. Such pharmaceutical compositions can be administered to mammals including humans. Also included in this invention are methods to deliver topically applied macromolecules into the tissue of mammals and methods of blocking the adhesion cascade.

65 Claims, No Drawings

OTHER PUBLICATIONS

Collins & Ferrier, "Monosaccharides: Their Chemistry and Their Roles in Natural Products", (John Wiley & Sons), p. 4, (1995).

Ed. Sybil Parker, "McGraw–Hill Dictionary of Chemical Terms", (McGraw–Hill, Inc.), p. 278, (1984).

Lasky, *Annual Review of Biochemistry*, vol. 64:1B–139, (1995).

Dasgupta & Tang, "Modern Synthetic Carbohydrate Chemistry," (ACS–Short Course, Aug. 19–20, 1994, Washington D.C.).

PHARMACEUTICAL COMPOSITION OF COMPLEX CARBOHYDRATES AND ESSENTIAL OILS AND METHODS OF USING THE SAME

BACKGROUND AND FIELD OF THE INVENTION

Complex carbohydrates, for purposes of this invention are defined as any polymer comprising more than two sugar moieties and would thus include such classes of and oliosaccharides. Polysaccharides include glycosaminoglycans and mannans whereas oligosaccharides are inclusive of sialylated sugars such as milk sugars.

Glycosaminoglycans can be obtained from numerous sources {e.g. rooster combs, trachea, umbilical cords, skin, articular fluids and certain bacteria such as Streptococci spp). Most glycosaminoglycans (hyaluronic acid, chondroitin sulfates A, B, and C, heparin sulfate, heparin, keratan sulfate, dermatan sulfate, etc.) are composed of repeating sugars such as non-sulfated N-acetylglucosamine, glucuronic acid and n-acetyl galactosamine (these are known as non-sulfated glycosaminoglycans) or polysulfated sugars (sulfated glycosaminoglycans).

Mannans are mannose-based polysaccharides which are normally extracted from plants. The most noteworthy is acemannan which is a beta 1,4-linked acetylated mannan extracted from the Aloe Vera plant (Aloe barbadensis Miller). This plant has been thought for centuries to have certain healing powers. Not until the 1980s was the active ingredient isolated and proven to have an effect on the immune system (see J. Pharm. Sci., 73 (1), January 1984).

Sialylated sugars are oligosaccharides which contain sialyl groups (e.g. sialic acid). They often contain fucose and may be significant components in the inflammatory process. Sialyl Lewis$^x$ and its derivatives are examples from this group (Tyrell et al, Proc. Natl. Acad. Sci. USA, 88, November 1991). At present, this oligosaccharide is so difficult to prepare/obtain that the cost ($4,600,000/g as listed by Oxford Glycosystems) limits research activities to determine its mechanism of action. Some of the milk sugars (also called hexaoses) are also incorporated in this general class of compounds. Examples of these are difucosyllacto-N-hexaose a and b, Disialyl-monofucosyllacto-N-hexaose, monofucosyllacto-N-hexsaose I, II, and II (obtainable from Oxford Glycosystems, Inc.).

Heparin, hyaluronic acid and chondroitin sulfate have been used therapeutically for several years. Heparin has been used for a number of years as an anticoagulant. Hyaluronic acid has been used therapeutically for several years as a replacement for the vitreous humor of the eye post surgery and, more recently, as replacement for joint fluid in arthritic joints. An extensive discussion of its various utilities is found in U.S. Pat. No. 4,141,973 to Balazs. The mode of action for hyaluronic acid injected directly into joints for treatment of arthritis has been proposed to be lubrication and replacement of the degraded joint fluid with highly viscous hyaluronic acid (see J. Bone Jt. Surg. 54A, 1972). High molecular weight (>750,000 daltons) and high viscosity were reported to be critical. (For purposes of this patent, all molecular weights are expressed as daltons. The unit designation will not be added hereafter.)

In the 1980s, it was discovered that chondroitin sulfate, or polysulfated glycosaminoglycan (known by its commercial name as ADEQUAN) could be injected intramuscularly for reduction of pain and inflammation associated with arthrosis of horses. The mechanism of action of this glycosaminoglycan has been speculated to be inhibition of certain degradative enzymes present in the joint fluid which are up-regulated by trauma.

In 1989, it was discovered that intravenous, intramuscular or subcutaneous delivery of hyaluronic acid could reduce the pain of arthritis (U.S. Pat. No. 4,808,576 by Schultz et al) when the hyaluronic acid was delivered remote to the site of the arthritis (not into the joint). This patent specifically states that the hyaluronic acid is administered remote to the site, that the higher molecular weights are preferred for topical applications and that the hyaluronic acid must be of high purity (>99% pure hyaluronic acid). No mention is made of hyaluronic acid in combination with essential oils or use of other macromolecules such as complex carbohydrates.

The importance of high molecular weight for effectiveness of hyaluronic acid in the treatment of arthritis is emphasized by Balazs (U.S. Pat. No. 4,141,973) and in a publication by Howard and McIlraith (see The Compendium, 15(3), March 1993) who summarize several clinical studies conducted to determine the most efficacious molecular weight range of hyaluronic acid injected intra-articularly to treat traumatic arthritis in horses. The conclusion from these studies is that hyaluronic acid with a molecular weight below $1 \times 10^6$ is not as effective as hyaluronic acid with a molecular weight above this value. More recently, della Valle et al (U.S. Pat. No. 5,166,331) claimed that there are two distinct pharmacologically active molecular weight ranges of hyaluronic acid or salts thereof. These moieties are utilized separately (purified one from the other) and defined as 50,000–100,000 (Hylastine) and 500,000–730,000 (Hylectin). Hylastine is specified for use in wound healing while Hylectin is specified for use in ocular surgery.

Whereas Balazs (U.S. Pat. No. 4,141,973), Schultz (U.S. Pat. No. 4,808,576) and della Valle (U.S. Pat. No. 5,166,331) all specify use of highly purified hyaluronic acid and whereas Balazs (U.S. Pat. No. 4,141,973) discards the fractions containing hyaluronic acid or their salts having molecular weights less than 750,000; and whereas della Valle (U.S. Pat. No. 5,166,331) discards impurities having molecular weights less than 30,000 and does not use hyaluronic acid with molecular weights between 100,000 and 500,000 and, thus, specifies use of clearly-defined molecular weights of hyaluronic acid for topical or ocular use; and whereas Schultz prefers use of hyaluronic acid with a molecular weight between $1.2 \times 10^6$ and $4.0 \times 10^6$ in topical formulations, we have discovered that all molecular weights of hyaluronic acids or salts thereof and all purities of this polymer are useful in topical preparations when mixed with essential oils for the treatment of various medical problems. The low purity hyaluronic acid or salt thereof useful in this invention (<98% pure hyaluronic acid) can be of a cosmetic grade which can contain up to 5% contaminants such as proteins, nucleic acids, teichoic acids and even endotoxins. Such material would not pass the owl monkey eye test used to select high purity hyaluronic acids and salts thereof (described by Balazs in U.S. Pat. No. 4.141.973) in that it would produce an inflammatory response in the eye. It also would not pass the horse joint injection test described by Schultz et al (U.S. Pat. No. 4,808,576). However, it does not produce a reaction when applied to the skin of mammals including humans, dogs, cats, horses, cattle, swine, rabbits, guinea pigs and mice.

Essential oils are natural components of plants which are extracted by various methods known to the art. They are generally very complex, containing numerous compounds (see Perfumer and Flavorist, 17, November/December 1992). More recently, some of the essential oils have been chemically synthesized. Most uses of these oils are as flavorings for foods and candies and as bath, cosmetic and perfume ingredients to provide pleasant aromas.

Some of the essential oils, also known as volatile oils, such as Rosemary Oil, Anise Oil, Cinnamon Oil, Clove Oil, Lemon Oil and Cardamom Oil have been shown to have limited antibacterial activity (see Elkhoully et al, 1980, Aust. J. Pharm. Sci., 9(3) September 1980 and Pharm. Acta Helv., 66(9–10) 1991). However, this activity was minimal when compared with a preservative used in current pharmaceuticals.

Several of the essential oils (i.e. Menthol, Eucalyptus Oil, Camphor, Peppermint Oil and Wintergreen Oil) are currently used in over-the-counter topical preparations such as BenGay, Mineral Ice, Flexall 454, etc. at concentrations as high as 30%. These topical medications claim pain relief but, according to FDA, act to relieve pain by producing a counterirritation, not by penetrating the skin and acting systemically to reduce inflammation and swelling which are the causes of pain. Also, these medications do not claim to reduce bruising, deep pain, itching, or induce wound healing. It has been noted by Williams and Barry (1989, Internat. J. Pharm., 57, 1989) that some essential oils such as chenopodium, eucalyptus, anise and ylang ylang oils penetrate the skin.

The inflammatory response is becoming better understood and has recently been summarized by Adams and Shaw (The Lancet, 343, Apr. 2, 1994). In their explanation, an adhesion cascade is stimulated when trauma occurs. This adhesion cascade is divided into four sequential steps of tethering, triggering, strong adhesion and motility. Tethering interactions are mediated by a family of three lectin-like carbohydrate-binding molecules (selectins). These interactions are strong enough to cause the leucocytes to roll along the blood vessel walls instead of flowing freely through such vessels, but not strong enough to cause these leucocytes to slow down. The triggering response is stimulated by factors such as cytokines and mediated by adhesion molecules called integrins. Integrins, by themselves, do not bind well to epithelium. However, when activated, integrins promote strong adhesion of the leucocyte to the epithelial surface. Leucocytes bind to the epithelial cells via their receptor sites such as CD44, CD31, etc. (see below). During strong adhesion, the interaction of these integrins with their ligands on the surface of the leucocytes are responsible for cessation of movement and flattening of the leucocyte. Finally, a process involving VCAM-1 and LFA-1 and other such integrins allows leucocytes to pass between endothelial cell junctions and into the tissue which has been traumatized. Collection of leucocytes at the site of trauma produces inflammation which is then followed by pain.

Previously, Shimitzu, et al (J. Immunol., 143, 1989) and Denning et al (J. Immunol. 144, 1990) determined that all leucocytes contain a receptor for hyaluronate which they named CD44. This receptor also binds chondroitin sulfate to a lesser extent and some other glycosaminoglycans. According to Munro et al (Am. J. Path, 141(6), December 1992) a ligand for E-selectin found on many or all leucocytes is a sialylated, polylactosamine containing a fucose moiety called Sialyl-Lewis$^x$. This ligand seems to be specifically expressed during the process of inflammation and its blockage could be significant in inhibiting the inflammatory process. Other receptors which bind to various macromolecules and complex carbohydrates have also been identified.

OBJECTS AND SUMMARY OF THE INVENTION

Although not bound by any theory, this invention describes a mechanism by which inflammation, resulting in pain and/or itching, is produced and methods to inhibit such inflammation, pain and/or itching by applying molecules (hereinafter referred to as compounds) which attach to the various receptor sites on the leucocytes, such as CD44, effectively blocking the adhesion cascade described above. Such blocking compounds are defined as any molecule which is biospecific for the adhesion cascade (adhesion-biospecific) and which interacts with receptor sites on blood cells or with the epithelial surface to inhibit adhesion of the leucocyte to the epithelium during migration and extravasation to a site of trauma. The adhesion cascade is defined as the mechanism by which inflammation is produced. The delivery of these compounds to the site of trauma is accomplished by parenteral injection of said compounds, by topical application of said compounds whereby the compounds are combined with essential oils, or by oral delivery of said compounds whereby the compounds are coated with protective oral delivery materials such as hydrogels, carbopols, etc.

More specifically, by this invention, we have discovered that even macromolecules such as complex carbohydrates (including polysaccharides, glycosaminoglycans, sialylated sugars, milk sugars and mannans), when mixed with minimal amounts of essential oils, reduce inflammation, pain, burning, swelling, itching, bruising, and induce wound healing. It is a further advantage of this invention that ultrapure or purified complex carbohydrates do not need to be utilized. Therefore, cosmetic grade hyaluronic acid or other normally-extracted polysaccharides are acceptable for use to treat the above conditions if they are applied topically or orally. It is an additional discovery that all sizes of polysaccharides are effective in this invention. Therefore, hyaluronic acids of molecular weights <30,000 and between 100,000 and 500,000 are effective and non-reactive. It is a further discovery that essential oils can be used to topically deliver macromolecules (molecules with a molecular weight >1000) into the dermal tissue and, consequently, into the blood stream. Finally, it has been discovered that the adhesion cascade which when stimulated by trauma results in inflammation, pain, swelling and/or itching, can be blocked by delivering any adhesion-biospecific compound according to this invention. Therefore, it has unexpectedly been found that essential oils when formulated with adhesion-biospecific compounds, such as complex carbohydrates, polysaccharides, oligosaccharides, sialylated sugars, or even monoclonal antibodies specific for the adhesion cascade, can effectively treat trauma, irritation, inflammation, swelling, burning, bruising, itching and induce wound healing in mammals when applied topically. Neither the complex carbohydrates nor the essential oils alone, when administered topically on the site of pain and inflammation, have a therapeutic effect. However, when combined in the mixtures described herein, there is a definite therapeutic effect.

This invention describes a composition of matter comprising at least one complex carbohydrate and at least one essential oil and also the method for effecting transdermal migration resulting in topical delivery of compounds, including macromolecules, through the skin of mammals and into the bloodstream by combining such compounds with essential oils. Macromolecules as used herein means any molecule with a molecular weight >1000. Mammals as used herein includes humans, dogs, cats, horses, cattle, swine, rabbits, guinea pigs, mice, and all other animals. This invention describes a method for inhibiting the progression of the adhesion cascade by use of compounds which bind to the biospecific receptor sites on leucocytes or on the epithelial surface and block the cascade. It also describes the method of treatment of inflammation, pain, burning, itching and bruising by use of a combination comprising at least one compound biospecific for blocking the adhesion cascade. Additionally, the invention describes a method for promoting granulation of wounds resulting in wound healing. Finally, the invention describes a process for reducing the seguelae of trauma in irritated or inflamed tissue of mammals by the topical application of a mixture of an essential oil or oils and an adhesion-biospecific compound such as a complex carbohydrate or mixture thereof. The pharmaceutical composition described is applied directly on or over the traumatized site. Particularly amenable conditions for such treatment are irritated or inflamed muscles, cramped muscles, inflamed tendons, swollen and painful joints, bruised tissue, tired feet, allergic conditions of the skin, open wounds, burns, sunburns, and decubitus ulcers.

DETAILED DESCRIPTION OF THE INVENTION

As discussed above, there have been no previous investigations describing use of complex carbohydrates such as polysaccharides in combination with essential oils to treat irritation, inflammation, swelling, pain, burning, bruising, itching or induce wound healing. A previous discussion of topical preparations containing hyaluronic acid or salts thereof was directed to utilizing specific fractions of this specific glycosaminoglycan. In fact, these fractions are described as vehicles for carrying active ingredient drugs and not themselves being the active ingredient. Francesco della Valle, et al (U.S. Pat. No. 5,166,331) isolated and characterized these two new fractions of hyaluronic acid, one having a low molecular weight of between 50,000 and 100,000 and one having a medium molecular weight of between 500,000 and 730,000, both being of high purity which is defined as not having inflammatory activity in the monkey eye test. The ultrapure hyaluronic acid of Schultz et al ($1.2 \times 10^6$–$4.0 \times 10^6$) is defined as >99% pure hyaluronic acid or salts thereof and as not producing inflammation when injected into the joints of horses. It is not expected that compounds such as complex carbohydrates of all molecular weight ranges and of low purity, could, when combined with essential oils, produce a pharmaceutical composition which effectively penetrates the skin, treats such varied conditions as inflammation, swelling, pain, burning, bruising, itching and induce wound healing without producing adverse reactions.

The use of complex carbohydrates of low purity and all molecular weight ranges including hyaluronic acid with a molecular weight of <30,000 and with molecular weights between 100,000 and 500,000 is a significant advantage of this invention since such material is relatively inexpensive. For instance, cosmetic grade hyaluronic acid which is of low purity (containing up to 5% impurities such as proteins, nucleic acids, teichoic acids and endotoxins) costs approximately $3,000/Kg whereas high purity pharmaceutical grade hyaluronic acid required for injection into mammals costs at least $150,000/Kg and contains less than 0.5% impurities. Low purity complex carbohydrates such as polysaccharides may be contaminated with up to 5% wt/vol proteins, 5% wt/vol nucleic acids, 1% wt/vol teichoic acids, 5% wt/vol lipids, fractions of hyaluronic acid <30,000 (defined as reactive by both Balazs in U.S. Pat. No. 4,141,973 and della Valle in U.S. Pat. No. 5,166,331), 5% wt/vol endotoxins and other small molecules. They will cause reactions when injected into monkey eyes or joints of horses but will not cause reactions when applied to the skin of mammals or when delivered orally to such mammals. Because the pharmaceutical compositions of this invention are applied topically or orally, these contaminants produce no adverse reactions (e.g. irritation or blistering of skin). Additionally, if one must select and use only certain molecular weight ranges of hyaluronic acid or salts thereof, the cost would be even higher. Therefore, products affordable for over-the-counter use can be formulated according to this invention whereas they could not be affordable if high purity components would be required.

The complex carbohydrates useful in combination with essential oils for direct topical application on sites of trauma may be of any type already recognized as useful for parenteral treatment. Additionally, adhesion-biospecific compounds such as complex carbohydrates and polysaccharides or their derivatives which bind to leucocyte receptor sites and/or bind to selecting, integrins, or any other receptor sites which are involved with the mechanism by which leucocytes move to sites of trauma and which, when bound, serve to inhibit any of the steps of the adhesion cascade (inflammatory process) would be useful in such pharmaceutical compositions. Such compounds may be obtained from any source. They can be extracted from rooster combs (U.S. Pat. No. 4,141,973), produced by fermentation of bacteria (U.S. Pat. No. 4,782,046), or extracted from trachea, skin, umbilical cords, etc. and should be pure enough to be used as a cosmetic in that they do not cause reactions when administered topically. These molecules include but are not limited to polysaccharides, glycosaminoglycans such as hyaluronic acids and derivatives or salts thereof (Genzyme, Lifecore Biomedicals, Meiji Seika Kaisha, Ltd.), chondroitin sulfates A, B, or C or their derivatives (SIGMA Chemical Company), keratan sulfate and derivatives thereof (SIGMA Chemical Company), heparin or heparin sulfate and derivatives thereof (SIGMA Chemical Company, Rhone Poulenc Rorer Pharmaceuticals), dermatan sulfate and derivatives thereof (SIGMA Chemical Company), mannans and derivatives thereof (SIGMA Chemical Company), acemannan (Carrington Laboratories) and derivatives thereof, extracts of the Aloe Vera plant and derivatives thereof (Aloe Vera gel concentrate supplied by Lily of the Desert, Irving, Tex.) and certain sialylated sugars such as trifucosyllacto-N-hexaose and sialyl Lewis$^x$ (Oxford Glycosystems). The sources listed are exemplary only and not limitations of the invention.

It is a preferred embodiment of this invention that at least two complex carbohydrates be included in the pharmaceutical composition. At least one should be from a low molecular weight range {from 1000 to <50,000 (e.g. 49,000)} and the other one or more should be from a higher molecular weight range (from 100,000 to 500,000 or >750,000). Such complex carbohydrates may or may not be a mixture of two or more different types of complex carbohydrates. For instance, one complex carbohydrate providing the high molecular weight moiety could be selected from the group consisting of hyaluronic acid and mannans and another complex carbohydrate in the same pharmaceutical composition providing the low molecular weight moiety could be a second polysaccharide or a sialylated sugar selected from the group consisting of chondroitin sulfate, keratan sulfate, heparin, heparin sulfate, dermatan sulfate, acemannan, sialyl Lewis$^x$, and hexaoses. Additionally, two different molecular weight ranges of a single type of complex carbohydrate could be incorporated in the pharmaceutical composition of this invention. The latter could occur if one prepared two different size polymers of the same compound. Therefore, the pharmaceutical composition could contain high and low molecular weight moieties of hyaluronic acid or salts thereof. These molecular weight moieties would be combined such that either the low molecular weight fast-acting or high molecular weight long-acting advantages of use would be the focus of the pharmaceutical composition. A more preferred embodiment would comprise a mixture of at least two polysaccharides in the pharmaceutical composition. One of these polysaccharides would be of a molecular weight range of <50,000 (e.g. 1000–49,000) and one polysaccharide would be of a molecular weight >750,000. An even more preferred embodiment of this invention comprises a mixture of equal parts of at least two polysaccharides. One of the polysaccharides would be of a low molecular weight range (<30,000). The second polysaccharide would of be a high molecular weight hyaluronic acid or salt or derivative thereof (>750,000). The most preferred embodiment of this invention comprises equal amounts of two or more molecular weight ranges of hyaluronic acid or salts or derivatives thereof. Such a composition would comprise for instance, a hyaluronic acid or salt or derivative thereof with a molecular weight of <50,000 combined with a hyaluronic acid or salt or derivative thereof which has a molecular weight >750,000.

When Aloe Vera is used to supply the complex carbohydrate, it is used as the base ingredient at a concentration of between 50% and 99% vol/vol Aloe Vera gel concentrate. A second complex carbohydrate such as a polysaccharide can be added to a concentration up to 5.0% wt/vol. This is then combined with an essential oil at a concentration of between 0.1% vol/vol and 20% vol/vol. The remaining portion of the formulation would be distilled deionized water (DI) and/or a cream or ointment base. A preferred embodiment comprises a 50% to 99% vol/vol Aloe Vera gel concentrate combined with a complex carbohydrate such as a polysaccharide at a concentration of between 0.01% and 5.0% wt/vol and an essential oil at a concentration of between 0.5% and 10.0% vol/vol. The remaining portion of the formulation would be DI water and/or a cream or ointment base. A more preferred embodiment of an Aloe Vera-containing formulation comprises 95% to 99% vol/vol Aloe Vera gel concentrate combined with hyaluronic acid at a concentration between 0.01% and 3.0% vol/vol and an essential oil at a concentration of between 0.5% and 5.0% vol/vol, the remainder being DI water. The most preferred embodiment of this formulation comprises a 98% vol/vol Aloe Vera gel concentrate (99% pure) as a base combined with high molecular weight hyaluronic acid at a concentration of between 0.1% and 1.0% vol/vol and an essential oil at a concentration between 1.0% and 3.0% vol/vol, the remainder being DI water. The essential oils would be selected from the group comprising Tea Tree Oil, Rosemary Oil, Oil of Wintergreen, Eucalyptus Oil, Camphor Oil and Menthol.

Unlike the essential oils used in current over-the-counter products and described in the above-mentioned publications, the essential oils used in this invention are incorporated into the formulation at minimal levels. The concentrations used are generally from 0.1% to 20% vol/vol with a preferred embodiment containing from 0.5% to 10% vol/vol of such oils. A more preferred embodiment comprises a formulation containing a total concentration of 1.0% to 5.0% vol/vol essential oils. The most preferred embodiment comprises a formulation containing a total concentration of 1.0% to 3.0% vol/vol essential oils. The essential oils of the invention may be either natural or synthetic and may be obtained from any source. For instance, natural Eucalyptus Oil, Rosemary Oil, Pine Needle Oil, Tea Tree Oil, Sage Oil, Jojoba Oil, Cinnamon Oil, Anise Oil, Lemon oil, Lime Oil, Orange Oil, Peppermint Oil, Spearmint Oil, Wintergreen Oil, Clove Leaf Oil, Almond Oil, White Pine Oil, Camphor Oil, Cardamon Oil, Cedar Leaf Oil and many others can be purchased from Lorann Oils. Synthetic Wintergreen Oil, Anise Oil, Fir Tree Oil, Rose Oil and Camphor Oil can be obtained from the same source. Menthol and derivatives thereof can be obtained from SIGMA Chemical Company. The purity of these essential oils is of little concern as long as they meet the requirements for a cosmetic and do not produce adverse reactions when applied to the skin of mammals.

We do not wish to be bound by any theory but we believe that the essential oils in our formulations are also acting as preservatives. Such oils, when added in concentrations between 0.1% and 20% vol/vol appear to inhibit the growth of bacteria and fungi in the preparations described herein. Therefore, the addition of preservatives such as parabens which are used in many pharmaceutical products may not be necessary for use in the pharmaceutical compositions of this invention.

The formulation of a complex carbohydrate with a natural or synthetic essential oil should be adequate to form an emulsion, suspension, solution, cream or ointment at the time of application. A liquid formulation will not be effective if the oil is separated from the aqueous phase. However, a suspension or solution which may be resuspended by shaking prior to application is acceptable for use. Any cream or ointment base which does not interfere with the effectiveness of the active ingredients may be included in the formulation. Therefore, one embodiment of this invention is a cream base containing at least one complex carbohydrate and at least one essential oil. Another embodiment is an ointment base containing at least one complex carbohydrate and at least one essential oil. Yet another embodiment of the invention is an Aloe Vera base containing at least one complex carbohydrate and at least one essential oil. However, the preferred embodiment is a liquid formulation in an aqueous base which contains at least one complex carbohydrate and at least one essential oil. A significant advantage of this liquid formulation is that the preparation is not greasy or oily, does not leave a greasy or oily film on the skin and does not leave a lingering odor on the skin.

The treatment of irritated or inflamed mammalian tissue by direct topical application requires a dose or total dose regimen effective to reduce or alleviate the results of the trauma. It is preferred to administer at least about 0.0005 mg/lb of body weight of each ingredient over the site of trauma at least once per day or as often as necessary. The components of this formulation are naturally-occurring substances and are safe when applied topically. It is believed that there is no inherent upper limit to the tolerable dose. However, as in all medicinal treatments it is prudent to use no more than is necessary to achieve the desired effect. It has been noted that more intense inflammation and pain require more dose applications for relief. A dose of 10 mg/lb of body weight has been used safely and could serve as an upper limit for use. Similar dose regimens are recommended for wound healing whereas the pharmaceutical composition is applied on the wound until adequate promotion of granulation of the wound has occurred and healing is complete.

A convenient topical application formulation is a combination of one or more complex carbohydrates such as mannans, polysaccharides, oligosaccharides, or Aloe Vera extracts at a total concentration of between 0.1% and 99% wt/vol with one or more essential oils at a total concentration of between 0.5% and 20% vol/vol with the remainder of the formulation being made up of a liquid, cream or ointment base. Another embodiment of the topical application formulation is a combination of one or more glycosaminoglycans at a total concentration of between 0.1% and 99% wt/vol with one or more essential oils at a total concentration of between 0.5% and 20% vol/vol with the remainder of the formulation being a cream, ointment or aqueous base. Another embodiment of the topical application formulation is a combination of one or more mannans at a total concentration of between 0.1% and 99% wt/vol with one or more essential oils at a total concentration of between 0.5% and 20% vol/vol, the remainder being a cream, ointment or aqueous base. A preferred embodiment of the invention is a combination of equal amounts of two or more polysaccharides of widely varying molecular weights (one below 30,000 and one above 500,000) at a combined concentration of between 0.5% and 3.0% wt/vol with two or more essential oils having a total concentration of between 0.5% and 5.0% vol/vol with the remainder of the formulation being an aqueous, cream or ointment base. A more preferred embodiment of the topical application formulation is a combination of one or more glycosaminoglycans or mannans (at least one with a molecular weight <30,000 and at least one with a molecular weight between 100,000 and 500,000 or >750,000) at a concentration of between 0.5% and 5.0% wt/vol and at least one essential oil at a total concentration of between 0.5% and 5.0% vol/vol with the remainder being DI water. An even more preferred embodiment of the topical application formulation is a combination of one glycosaminoglycan or mannan with a molecular weight <30,000 and one glycosaminoglycan or mannan with a molecular weight >750,000 (the total concentration of the polysaccharide component being between 0.5% and 3.0% wt/vol) and one or more essential oils with a total concentration of between 1.0% and 3.0% vol/vol, the remainder being DI water. The most preferred embodiment of the topical application formulation is a combination of hyaluronic acid with a molecular weight <30,000 with hyaluronic acid with a molecular weight between 100,000 and 500,000 or >750,000 at a total hyaluronic acid concentration of between 0.5% and 3.0% wt/vol and an essential oil selected from the group comprising Rosemary Oil, Tea Tree Oil, Wintergreen Oil, Eucalyptus Oil, Menthol and Camphor at a concentration of between 1.0% and 3.0% vol/vol with the remainder of the formulation being DI water. In order to provide the most effective, most acceptable (aroma and spreadability) and least expensive embodiment of this invention the formulation would contain 1.0% wt/vol hyaluronic acid (made up of equal volumes of low molecular weight hyaluronic acid and high molecular weight hyaluronic acid) combined with 2% wt/vol Tea Tree Oil and/or Wintergreen Oil with the remainder of the formulation being DI water.

Complex carbohydrates which we have specifically utilized in successful pharmaceutical compositions include heparin, hyaluronic acid, chondroitin sulfate, dermatan sulfate, keratan sulfate, and acemannan (active ingredient of Aloe Vera). Essential oils which we have specifically utilized in successful pharmaceutical compositions include Tea Tree Oil, Rosemary Oil, Eucalyptus Oil, Wintergreen Oil, Sage Oil, Jojoba Oil, White Pine Oil, Camphor Oil, Cinnamon oil, Oil of Clove and Menthol.

The present invention has been found to be particularly effective in the treatment of any type of inflammation, pain and/or itching which is associated with or biospecific for inhibition of the adhesion cascade defined and described earlier. It is preferable for: treatment of muscle and joint inflammation and pain resulting from athletic injuries, treatment of inflammation and pain associated with arthritis and bursitis, and relief from pain often referred to as "tired feet", reduction of inflammation (edema) in extremities resulting from diabetes, reduction of inflammation and pain in addition to wound healing of decubitus ulcers resulting from poor circulation by diabetic patients or bedridden patients, treatment of inflammation and itching of skin resulting from allergic reactions such as poison ivy and insect bites/stings, treatment of inflammation and pain associated with tendonitis, treatment of inflammation and pain associated with muscle cramps, inhibition of bruising and inflammation post trauma if applied immediately, dissolution of bruises which have already formed, wound healing in superficial cuts and scrapes as well as wound healing after surgery to reduce scarring, treatment of inflammatory skin conditions such as acne or psoriasis and treatment of dry skin, burns, or sunburn.

The invention described herein is for use with any mammal including but not limited to humans, dogs, cats, horses, cattle and swine.

The invention is further illustrated but is not intended to be limited by the following examples.

EXAMPLE 1

High molecular weight (>750,000) cosmetic grade hyaluronic acid obtained from Meiji Seika Kaisha, Ltd, was dissolved in distilled/deionized water (DI) to a concentration of from 1.1 to 1.5% wt/vol. This solution was treated with high pH and high temperature to break down the molecular weight to <30,000. The latter treatment involved raising the pH of the solution to 11.0 and mixing the hyaluronic acid at 37°–60° C. for at least 4 hours. The viscosity of a 1% solution measured at 37° C. in a Cannon-Manning Viscometer dropped from >1000 c/s to <10 c/s as a result of this treatment. This hyaluronic acid was adjusted to 1.0% wt/vol by dilution in DI water. The 1.0% hyaluronic acid solution was aliquoted into 10 vials with 100 mL each. Various essential oils were added to each vial at a concentration of 2.0% vol/vol. The resulting suspensions were mixed at room temperature for 2–3 hours. The following essential oils were tested in this experiment: Rosemary Oil, Tea Tree Oil, Camphor Oil, Oil of Wintergreen, Eucalyptus Oil, Cinnamon Oil, Sage Oil, Jojoba Oil, Lemon Oil and Oil of Clove. All of the essential oils were obtained from Lorann Oils. All preparations were held at 4° C. for 14 days after which they were evaluated for their suspension characteristics and for their sterility. Suspension characteristics were evaluated visually while sterility was evaluated by placing a 0.1 mL sample onto a blood agar plate, incubating the plate at 37° C. for 7 days and observing the plates for the presence of colonies.

The evaluation for sterility was conducted in order to determine whether any or all of the essential oils would show a preservative effect. Hyaluronic acid or salts thereof, when handled by the methods described, will normally show contamination under the conditions described.

Tea Tree Oil, Eucalyptus Oil and Camphor Oil produced the best suspensions. These suspensions remained stable while the others separated out with the oil either dropping out or rising to the top of the hyaluronic acid solution.

There were no colonies found on the blood agar plates except for the plate with the lemon oil combined with hyaluronic acid. This plate had two colonies of different types, the colonies being determined to be air contaminants. A retest plate from this preparation showed no colonies. It appears that all of the essential oils evaluated in this example demonstrated preservative activity. The preparation containing only hyaluronic acid and no essential oils was contaminated and showed 28 colonies on the blood agar plate.

Each suspension was remixed and aliquoted into 10 mL amounts in 25 mL vials. Five patients with localized chronic pain complaints were given one vial of each preparation over a period of 2 months. After using the first preparation, they were interviewed about effectiveness, safety (development of rashes or other adverse reactions), spreadability/feel and odor. Effectiveness was evaluated on a scale of 1 to 5 with 5 being the most effective (most relief of their condition). Safety was evaluated by noting any adverse effects. Spreadability was evaluated on a 1 to 3 scale with 3 being best. Odor was evaluated on a scale of 1 to 3. Pleasing was defined as 3 while unpleasing was given a value of 0. At this point, they were given the second preparation to evaluate. The third through 11th preparations were evaluated in the same manner. The 11th preparation contained hyaluronic acid without essential oils. Results are summarized in Table 1.

Interviews with all patients were positive in that all patients reported immediate relief within 5 minutes of applying the topical preparations. Two reported relief within 30 seconds of treatment. None of the patients reported that the hyaluronic acid alone was effective. None of the patients noticed untoward reactions. Spreadability was not ideal and most of the patients complained that the suspension was too thin and difficult to apply. However, they liked the fact that the preparations were not oily. The odor of the preparations were generally pleasing. Only Tea Tree Oil and Sage Oil produced "unpleasing" comments. All patients commented that even though the preparation had an odor at application, there was no residual odor noted within a few minutes after application.

The remaining vials of the various preparations were held at 4° C. to for up to 12 months to evaluate the long-term preservative effects of the various essential oils. Only the Lemon Oil, Cinnamon Oil and straight hyaluronic acid were found to be contaminated with bacteria or fungi. Since these preparations were not handled aseptically, it confirms that most of the essential oils have preservative activity. It should also be noted that preparations containing Tea Tree Oil or Wintergreen Oil have been held at room temperature for as long as 4 years with no contamination being noted upon evaluation via blood agar plates as described previously.

TABLE 1

EVALUATION OF COMBINATIONS OF ESSENTIAL OILS WITH LOW MOLECULAR WEIGHT HYALURONIC ACID

| Preparation (Oil) | Effectiveness | Safety | Spreadability | Odor |
|---|---|---|---|---|
| Rosemary | 5 | No Rxs | 2 | 3 |
| Tea Tree | 5 | No Rxs | 2 | 1.7 |
| Camphor | 4 | No Rxs | 1 | 3 |
| Wintergreen | 5 | No Rxs | 2 | 3 |
| Eucalyptus | 5 | No Rxs | 1.7 | 3 |
| Cinnamon | 4 | No Rxs | 2 | 3 |
| Sage | 4 | No Rxs | 1.7 | 1 |
| Jojoba | 4 | No Rxs | 1.7 | 1.7 |
| Lemon | 3 | No Rxs | 1.7 | 2 |
| Clove | 4 | No Rxs | 1.7 | 3 |
| None* | 0 | No Rxs | 2 | 3 |

*Control - Contains only hyaluronic acid with no essential oils
No Rxs = No reactions observed by patients
The Effectiveness, Spreadability and odor scores are averages of the 5 responses.

The medical complaints of the patients being treated in this study included:

1. Chronic knee pain/swelling post knee surgery for chondromalacia
2. Chronic knee pain/swelling as a result of torn cartilage
3. Chronic pain/swelling in first and second finger of right hand diagnosed as arthritis
4. Chronic foot pain (undiagnosed)
5. Chronic pain in left thumb/wrist post reconstructive surgery

EXAMPLE 2

High molecular weight (>750,000) cosmetic grade hyaluronic acid was obtained from Meiji Sieka Kaisha, Ltd. It was dissolved in distilled/deionized water (DI) to a concentration of 1.0 % wt/vol. The viscosity of this solution at 37° C. was >1000 c/s and the molecular weight was >750,000. The 1.0% hyaluronic acid solution was aliquoted into 10 vials with 100 mL each. Various essential oils were added to each vial at a concentration of 2.0% vol/vol. The resulting suspensions were mixed at room temperature for 2–3 hours. The following essential oils obtained from Lorann Oils were tested in this experiment: Rosemary Oil, Tea Tree Oil, Camphor Oil, Oil of Wintergreen, Eucalyptus Oil, Cinnamon Oil, Sage Oil, Jojoba Oil, Lemon Oil and Oil of Clove. All preparations were held at 4° C. for 7 days after which they were evaluated for their suspension characteristics and for sterility according to procedures described in EXAMPLE 1. All oils remained in suspension due to the viscosity of the hyaluronic acid. All of the preparations appeared sterile, again confirming the preservative activity of these oils. Each suspension was remixed and aliquoted into 10 mL amounts in 25 mL vials. The same five patients with localized chronic pain complaints who evaluated the preparations in EXAMPLE 1 evaluated these preparations. At the same time that they were given the vials in Example 1, they were given the corresponding vial from this example. They were instructed to compare the two preparations with the same essential oil (denoted by numbers). After using the first preparation, they were interviewed about effectiveness, safety (development of rashes or other adverse reactions), feel (spreadability) and odor. Effectiveness was evaluated on a scale of 1 to 5 with 5 being the most effective (most relief of condition). Safety was evaluated by noting any adverse effect. Spreadability was evaluated on a 1 to 3 scale with 3 being best. Odor was evaluated on a scale of 1 to 3. Pleasing was defined as 3 while unpleasing was defined as 0. At this point, they were given the second preparation to evaluate. The third through 11th preparations were evaluated in the same manner. Results are summarized in Table 2. All numbers shown in this table are averages of the responses.

Patients indicated that although these preparations were as effective as the preparations in EXAMPLE 1, it took from 45 to 60 minutes for the effect to be significant. However, they indicated that the effect lasted for 4–8 hours. The effectiveness of preparations in EXAMPLE 1 seemed to last only 1–3 hours. All patients liked the spreadability of the preparations in EXAMPLE 2. All except the Camphor Oil spread smoothly and left the skin feeling soft. The Camphor Oil seemed to absorb rapidly leaving the skin feeling dry. Again, no adverse reactions were noted.

The remaining vials were held at 4° C. for 6 months and evaluated for the presence of contaminating bacteria or fungi by inoculating blood agar plates with 0.1 mL from each sample. Only the Lemon Oil and Cinnamon oil mixtures and straight hyaluronic acid showed contamination. In these more viscous suspensions it again appears that most of the essential oils act as preservatives.

TABLE 2

EVALUATION OF A COMBINATION OF ESSENTIAL OILS WITH HIGH MOLECULAR WEIGHT HYALURONIC ACID

| Preparation (Oil) | Effectiveness | Safety | Spreadability | Odor |
|---|---|---|---|---|
| Rosemary | 4 | No Rxs | 3 | 3 |
| Tea Tree V | 4 | No Rxs | 3 | 1.7 |
| Camphor | 3 | No Rxs | 2 | 3 |
| Wintergreen | 4 | No Rxs | 3 | 3 |
| Eucalyptus | 4 | No Rxs | 3 | 3 |
| Cinnamon | 2 | No Rxs | 3 | 3 |
| Sage | 2 | No Rxs | 3 | 1 |
| Jojoba | 3 | No Rxs | 3 | 1.7 |
| Lemon | 2 | No Rxs | 3 | 2 |
| Clove | 2 | No Rxs | 3 | 3 |
| None* | 0 | No Rxs | 3 | 3 |

*Control - Contains only hyaluronic acid with no essential oils
No Rxs = No Reactions
Effectiveness, Spreadability and odor scores are averages of the 5 responses.

The complaints of the patients in this study included:
1. Chronic knee pain/swelling post knee surgery for chondromalacia
2. Chronic knee pain/swelling as a result of torn cartilage
3. Chronic pain/swelling in first and second finger of right hand diagnosed as arthritis
4. Chronic foot pain (undiagnosed)
5. Chronic pain in left thumb/wrist post reconstructive surgery

EXAMPLE 3

A 1.0% wt/vol solution of dermatan sulfate (chondroitin sulfate B obtained from SIGMA Chemical Company) was prepared using DI water. The viscosity of this preparation was <100 c/s. The molecular weight was 15,000. This preparation was mixed 1:1 with the 1.0% wt/vol high molecular weight hyaluronic acid solution described in EXAMPLE 2. Five aliquots of 30 mL each were dispensed into vials. To the first aliquot was added 2.0% vol/vol Rosemary Oil. To vials 2–4 were added either Eucalyptus Oil, Wintergreen Oil or Tea Tree Oil (all obtained from Lorrann Oils). No essential oils were added to the fifth vial. All preparations were held at 4° C. for 7 days after which they were evaluated for their suspension characteristics. All oils remained in suspension due to the viscosity of the hyaluronic acid. Each suspension was remixed and aliquoted into 10 mL amounts in 25 mL vials. Three patients with chronic pain/swelling complaints were given one vial of each preparation to evaluate. They were asked to compare effectiveness, safety, spreadability and odor. The same numerical scales for evaluation of these parameters were used as is noted in EXAMPLES 1 and 2. Results are listed in Table 3.

The general response was that all preparations provided relief within 5 minutes and such relief lasted up to 6 hours. Also, spreadability was totally acceptable to all patients. It appears that this combination is more effective than the lower molecular weight preparation described in EXAMPLE 1 in that it provides both quicker and longer-lasting relief from pain. The control preparations containing only the essential oils did not provide relief and were not acceptable for spreadability. The control which contained only the dermatan sulfate and hyaluronic acid components ("NONE") was not effective.

TABLE 3

COMPARISON OF MIXTURES CONTAINING DERMATAN SULFATE, HIGH MOLECULAR WEIGHT HYALURONIC ACID AND VARIOUS ESSENTIAL OILS

| Preparation (Oil) | Effectiveness | Safety | Spreadability | Odor |
|---|---|---|---|---|
| Rosemary | 5 | No Rxs | 3 | 3 |
| Eucalyptus | 5 | No Rxs | 3 | 3 |
| Wintergreen | 5 | No Rxs | 3 | 3 |
| Tea Tree | 5 | No Rxs | 3 | 1.7 |
| None* | 0 | No Rxs | 3 | 3 |
| Rosemary only** | 0 | No Rxs | 0 | 3 |
| Wintergreen Oil** | 0 | No Rxs | 0 | 3 |
| Tea Tree Oil** | 0 | No Rxs | 0 | 1.7 |

*Control - Contains only dermatan sulfate and hyaluronic acid with no essential oils
**Contains only the listed essential oil and no hyaluronic acid
No Rxs = No reactions
Numerical values for effectiveness, spreadability and odor are averages of the 3 responses.

The complaints of these patients included:
1. Chronic pain in left leg resulting from diagnosed osteoarthritis of the left hip
2. Chronic neck pain resulting from diagnosed stenosis and bone spur formation requiring surgery
3. Chronic tired feet (patient on feet on concrete floors all day)

EXAMPLE 4

In order to determine whether a combination of a high and low molecular weight mixture of a salt of hyaluronic acid would produce results similar to those described in EXAMPLE 3, the following experiment was conducted. High molecular weight (>750,000) cosmetic grade hyaluronic acid (obtained from Meiji Seika Kaisha, Ltd.) was prepared as in EXAMPLE 2. The concentration of this solution was adjusted to 1.0% wt/vol. The viscosity of this solution at 37° C. was >1000 c/s and the molecular weight was >750,000. Low molecular weight cosmetic grade hyaluronic acid (from the same source) was prepared as described in EXAMPLE 1. The resulting hyaluronic acid solution was adjusted to 1.0% wt/vol by dilution in DI water. Equal volumes of high molecular weight and low molecular weight hyaluronic acid solutions were mixed and aliquoted into 50 mL portions. To the first aliquot was added 2.0% vol/vol Rosemary Oil. To vials 2–4 were added either Eucalyptus Oil, Oil of Wintergreen or Tea Tree Oil, each at 2.0% vol/vol. No essential oils were added to the fifth vial. All preparations were held at 4° C. for 7 days after which they were evaluated for their suspension characteristics. All oils remained in suspension due to the viscosity of the hyaluronic acid solution. Each suspension was remixed and aliquoted into 10 mL amounts. Three patients with chronic pain/swelling complaints were given one vial of each preparation to evaluate. They were asked to compare effectiveness, safety, spreadability and odor. The same numerical scales for evaluation were used as noted in EXAMPLES 1–3. Again, the results are listed as averages of the three responses. Results are listed in TABLE 4.

The general response was that all preparations provided relief within 5 minutes and such relief lasted up to 6 hours. Also, spreadability was totally acceptable to all patients. It appears that this combination is as effective as a mixture of low molecular weight dermatan sulfate and high molecular weight hyaluronic acid in that it provides quicker and longer relief from pain. The control preparations containing only the hyaluronic acid (NONE *) did not provide relief. The control preparations containing only essential oils (Tea Tree Oil or Wintergreen Oil) did not provide relief.

Patients generally commented that the preparations were not oily upon application, a quality that all appreciated. Also, all patients commented that although there is some odor upon topical application, there is no residual odor—no odor could be detected by a few minutes after application.

TABLE 4

EVALUATION OF A MIXTURE OF HIGH AND LOW MOLECULAR WEIGHT HYALURONIC ACIDS

| Preparation (Oil) | Effectiveness | Safety | Spreadability | Odor |
|---|---|---|---|---|
| Rosemary | 5 | No Rxs | 3 | 3 |
| Eucalyptus | 5 | No Rxs | 3 | 3 |
| Wintergreen | 5 | No Rxs | 3 | 3 |
| Tea Tree | 5 | No Rxs | 3 | 1.7 |
| None* | 0 | No Rxs | 3 | 3 |
| Tea Tree** | 0 | No Rxs | 0 | 1 |
| Wintergreen** | 0 | No Rxs | 0 | 3 |

*Control - Contains only hyaluronic acids and no essential oils
**Contains only the essential oil listed but no hyaluronic acid
No Rxs = No reactions
Numerical scores for effectiveness, spreadability and odor are averages of the three responses The complaints of these patients included:
1. Chronic pain in left leg resulting from diagnosed osteoarthritis of the left hip
2. Chronic neck pain resulting from diagnosed stenosis and bone spur formation requiring surgery
3. Chronic tired feet (patient on feet on concrete floors all day)

EXAMPLE 5

Heparin sulfate has long been known as an anticoagulant when administered intramuscularly, intravenously or subcutaneously. However, to our knowledge it has never been used topically. Since dermatan sulfate and hyaluronic acid are topically effective when mixed with essential oils, it was of interest to determine whether heparin sulfate could also be topically effective. Heparin sulfate was purchased from Rhone Poulenc Rorer in liquid form at a concentration of 30 mg/0.3 mL. This preparation was diluted to 30 mg/mL (3.0% wt/vol) with DI water and aliquoted in 1.0 mL amounts. One percent vol/vol Rosemary Oil was added to one aliquot, 2.0% vol/vol Rosemary Oil was added to a second aliquot and 2.0% vol/vol Wintergreen Oil was added to a third aliquot. One aliquot contained no essential oils and was used as a control (Hep Only in TABLE 5). All essential oils were obtained from Lorann Oils.

These formulations were compared in their ability to treat various medical complaints. Patients were given one of each preparation and requested to evaluate the effectiveness of the preparations. Effectiveness was evaluated on the basis of good (G), fair (F) or poor (P). After use of the preparations for a period of at least one month, patients were interviewed as to their satisfaction with the products. Results of these interviews are presented in TABLE 5.

TABLE 5 indicates that Heparin sulfate mixed with essential oils appears to work effectively when applied topically to treat bruising, torn muscles, sprains and tendonitis. According to the interviews, the 1.0% solution may have had a slightly shorter effect with some of the more painful medical complaints. Heparin sulfate alone (without essential oils) had no effect when applied topically.

TABLE 5

ACCEPTABILITY OF HEPARIN/ESSENTIAL OIL MIXTURES

| Patient Complaint | Effectiveness | | | | Comments |
|---|---|---|---|---|---|
| | 1% R | 2% R | 2% TT | Hep Only | |
| Extensive bruise | G | | | | 4 cm × 8 cm bruise resolved much faster than normal |
| Torn muscle in rt. thigh | G | | | | Noticed short-term improvement, multiple applications necessary for resolution |
| Ankle sprain with bruising and swelling | | G | | | Bruise resolved in 3 days, ankle supported full weight in 2 days |
| Tendonitis - rt. elbow | | G | | | Required 3–4 treatments/day for 3 months for complete resolution |
| Torn muscle in left calf | | G | | | Patient supported full weight in 2 days |
| Chronic cramping of foot | | | G | | Cramps resolved within 1 minute and did not return for 4 hours |
| Acute muscle cramp-rt. calf | | | G | | Cramp was relieved within 30 seconds |
| Chronic knee pain: chondromalacia | | | | P | No Relief was noted |
| Torn muscle in rt. thigh | | | | P | No effect was noted. |

1% R = A mixture containing 3% heparin plus 1% Rosemary Oil
2% R = A mixture containing 3% heparin plus 2% Rosemary Oil
2% TT = A mixture containing 3% heparin plus 2% Tea Tree Oil
Hep only = Control - A mixture containing 3% heparin without an essential oil

EXAMPLE 6

In order to determine the effect of an extract of the Aloe Vera plant, Aloe Vera gel concentrate which has acemannan as one of its active ingredients, was obtained from Lily of the Desert. Thirty milliliter aliquots of this Aloe Vera gel concentrate (99.0% pure) were placed into vials. To one aliquot was added 1.0% vol/vol Wintergreen Oil, to a second aliquot was added 2.0% vol/vol Wintergreen oil, to a third aliquot was added 2.0% vol/vol Tea Tree Oil, to a fourth aliquot was added 2.0% vol/vol Rosemary Oil and to a 5th aliquot was added 2.0% vol/vol Eucalyptus Oil. One aliquot contained no oil and was used as a control (NONE * in TABLE 6). All aliquots were held at 4° C. for 7 days after which they were evaluated for their suspension characteristics. Sterility was also evaluated by placing 0.1 mL samples from each preparation onto a blood agar plate. The plates were incubated at 37° C. for 7 days after which they were observed for the presence of colonies. All oils remained in suspension due to the viscosity of the Aloe Vera gel concentrate. All of the preparations were sterile. Each suspension was remixed and aliquoted into 10 mL amounts. Three patients with chronic problems resulting in pain and swelling were given one vial of each preparation to evaluate. They were asked to compare effectiveness, safety, spreadability and odor. The same numerical scales for evaluation of these parameters were used as described previously in EXAMPLE 1. Results are listed in TABLE 6. All numerical values are averages of the responses of the 3 patients.

TABLE 6

EVALUATION OF A MIXTURE OF ALOE VERA AND ESSENTIAL OILS

| Preparation (Oil) | Effectiveness | Safety | Spreadability | Odor |
| --- | --- | --- | --- | --- |
| Tea Tree | 4 | No Rxs | 1.7 | 1 |
| Wintergreen 1% | 3 | No Rxs | 1.7 | 3 |
| Wintergreen 2% | 4 | No Rxs | 1.7 | 3 |
| Rosemary | 4 | No Rxs | 1.7 | 3 |
| Eucalyptus | 4 | No Rxs | 1.7 | 3 |
| None* | 0 | No Rxs | 1.7 | 3 |

*Control - Contains Aloe Vera Only -- no essential oil added
No Rxs = No reactions
Numerical values for effectiveness, spreadability and odor are averages of the 3 responses The complaints of the patients in this study included:
1. Acute tendonitis of the right elbow
2. Torn muscle in the right calf
3. Chronic knee pain/swelling as a result of torn cartilage Patients indicated that all preparations produced equivalent results reducing pain and swelling. The positive effects were noted within 5 minutes and lasted for 2–4 hours. Spreadability was acceptable to all patients. None of the preparations produced adverse reactions. The control preparation containing only the Aloe Vera gel concentrate was ineffective.

EXAMPLE 7

An 83 year old male suffering from terminal colon cancer was bedridden for 5 months. The family of caregivers was informed that bedsores would be a major problem for the patient and that they should notify the hospice nurses when such condition began to develop. Hospice nurses checked the patient two times per week during the first three months of the patient's incapacitation. Later, the Hospice nurses visited three days per week checking on the patient's well-being. The patient was given a combination of low and high molecular weight hyaluronic acids formulated with Oil of Wintergreen (prepared as in EXAMPLE 4) as a preventative before any indication of bedsores was noted. Areas of the body which appeared reddened from pressure (e.g. buttocks, rib cage on back and shoulder blades) were massaged with the formulation once or twice per day (depending on the patient's tolerance to movement). The patient never developed bedsores. It should be noted that the patient was not routinely turned as suggested by the nurses because this procedure was too painful. Therefore, the development of bedsores was expected. The Hospice nurses were amazed and commented repeatedly about the use of the formulation to prevent bedsores.

EXAMPLE 8

A 93 year old male who was bedridden as a result of Alzheimer's disease for 1.5 years was treated with a formulation containing 2.0% Rosemary Oil (Rosemary Oil was obtained from Lorann Oils) and 1.0% dermatan sulfate (chondroitan sulfate B obtained from SIGMA Chemical Company) for one year while at home. The treatment included massaging the buttocks, back and shoulders with the formulation once or twice per day. During this period of treatment the patient developed no bedsores. After transfer to a nursing home which did not allow the use of the formulation, the patient developed bedsores within 2 weeks. He had continuing problems with such ulcers until his death.

EXAMPLE 9

A 45 year old female who is extremely sensitive to poison ivy was given a formulation containing a combination of 1.0% wt/vol high molecular weight hyaluronic acid (400,000–500,000) and 2.0% Rosemary Oil to use on an active case of poison ivy. The formulation was prepared by using hyaluronic acid obtained from LIPO CHEMICALS, INC. and Rosemary Oil obtained from Lorann Oils. Other topical treatments such as Benadryl, Dermarest, Hydrocortisone 0.5%, etc. provided only temporary relief and the dermatitis with weeping pustules remained active. The individual is so sensitive that poison ivy desensitization injections are not tolerated. This individual reported that topical use of the hyaluronic acid combined with Rosemary Oil applied directly onto the weeping pustules caused an initial stinging but that relief from itching occurred "within minutes". The relief was temporary as with cortisone creams. However, she reported that the pustules dried up and resolved "within a few days". In the past this individual noted that the poison ivy pustules would remain up to 6 weeks.

EXAMPLE 10

A 57 year old bedridden diabetic patient suffering from edema of the lower extremities complicated by chronic problems with decubitus ulcers obtained one of the formulations of this invention to try. This patient was given a formulation containing a combination of 1.0% wt/vol high molecular weight hyaluronic acid and 1.0% wt/vol dermatan sulfate (in a 1:1 ratio) formulated with 2.0% vol/vol Oil of Wintergreen. The hyaluronic acid for this formulation was obtained from Genzyme, Inc., the Dermatan sulfate was obtained from SIGMA Chemical Company and the essential oils were obtained from Lorann Oils. The preparation was applied three times per day onto the decubitus ulcers and generally onto the lower extremities. The patient reported that within one week the edema was resolved and the ulcers were healing. Within one month he was out of bed and back to work. This was a significant improvement since he had not been able to work for 6 months. This patient has continued to use this formulation over a two year time period with no adverse side effects and no return of his condition.

EXAMPLE 11

A 27 year old female with chronic acne since puberty was given a preparation containing 1.0% wt/vol hyaluronic acid in combination with 1.0% vol/vol Wintergreen Oil. The molecular weight of the hyaluronic acid used to formulate this preparation was obtained from Genzyme, Inc. and had a molecular weight of between 550,000 and 650,000. The Wintergreen Oil was obtained from Lorann Oils. This individual applied the preparation twice per day (morning and evening). After 2 weeks she reported a significant improvement in healing of the active eruptions and also reported smoothing of the skin. After one month she reported that her face was free of eruptions and that the skin felt smoother than ever before. This individual has continued using the preparation for 2 years without return of her acne problem and without development of any adverse reactions.

EXAMPLE 12

A preparation containing 99% Aloe Vera gel concentrate (obtained as 99% pure from Lily of the Desert) to which was added 2.0% vol/vol Wintergreen Oil (obtained from Lorann Oils) and 0.2% vol/vol high molecular weight (>750,000) hyaluronic acid (obtained from Lifecore Biomedical, Inc.)

was given to three individuals suffering from knee problems involving pain and swelling. The first patient had been diagnosed with chondromalacia, the second patient with torn cartilage and the third patient had been diagnosed with osteoarthritis. Each patient used the preparation for a period of one month after which they were interviewed about the effectiveness, safety and spreadability of the formulation. The responses are summarized in TABLE 7.

Each of the patients commented that they were impressed that the preparation was not oily and that there was no lingering odor after topical application.

TABLE 7

SUMMARY OF RESULTS ON USE OF A COMBINATION OF ALOE VERA, OIL OF WINTERGREEN AND HYALURONIC ACID TO TREAT PAIN AND SWELLING ASSOCIATED WITH KNEE PROBLEMS

| Diagnosis | Effectiveness | Safety | Spreadability |
|---|---|---|---|
| Chondromalacia | Excellent at a use rate of 3 applications/day | No Reactions | Too thin |
| Torn cartilage | Good - relief for 1–2 hours after treatment | No Reactions | Would prefer something thicker |
| Osteoarthritis | Excellent at a use rate of 2 applications/day | No Reactions | Excellent results |

EXAMPLE 13

A preparation containing 99% pure Aloe Vera gel concentrate (obtained as 99% pure from Lily of the Desert) to which was added 2% vol/vol Tea Tree Oil (obtained from Lorann Oils) and 0.2% vol/vol high molecular weight hyaluronic acid (>750,000 obtained from Lifecore Biomedical) was given to four patients suffering from three different maladies. Patient No. 1 was a 42 year old female who had been diagnosed with tendonitis. Patient No. 2 was a 39 year old male who had torn a muscle in his left calf. Patient No. 3 was a 59 year old male who had fallen off a horse and was complaining of stiffness and pain in the lower back. Patient No. 4 was a 38 year old female who had to stand all day on concrete floors and suffered from a chronic "tired feet" syndrome. Each patient was instructed to use the preparation for one month and report results of effectiveness, safety and general comments during an interview. The results of these interviews are summarized in TABLE 8.

All patients reported excellent to good results. Additionally, all patients commented that they liked not having an oily or greasy medicament. Additionally, these individuals liked the lack of residual odor after topical application.

TABLE 8

SUMMARY OF INTERVIEWS WITH PATIENTS USING A PREPARATION CONTAINING AN ALOE VERA/TEA TREE OIL MIXTURE

| Complaint | Effectiveness | Safety | Comments |
|---|---|---|---|
| Tendonitis | Good | No reactions | Requires multiple treatments/day to obtain significant relief |

TABLE 8-continued

SUMMARY OF INTERVIEWS WITH PATIENTS USING A PREPARATION CONTAINING AN ALOE VERA/TEA TREE OIL MIXTURE

| Complaint | Effectiveness | Safety | Comments |
|---|---|---|---|
| Torn muscle in left calf | Excellent | No reactions | Patient was able to walk normally within 7 days |
| Back pain and stiffness | Excellent | No reactions | Immediate relief noted after application. Treatment was only required for 5 days |
| Chronic tired feet | Excellent | No reactions | Relief occurred within 1 min. after application |

EXAMPLE 14

A preparation containing a 1:1 ratio of 1.0% wt/vol low molecular weight hyaluronic acid (prepared from a liquid 1.0% solution obtained from Lifecore Biomedical and treated according to the description in EXAMPLE 1 to produce a molecular weight of <30,000) and 1.0% wt/vol high molecular weight hyaluronic acid (obtained from Lifecore Biomedical and containing a molecular weight >500,000) and 2.0% vol/vol Rosemary Oil (obtained from Lorann Oils) was provided to two patients with diagnosed psoriasis. The patients were instructed to use the preparation for one month and report their results during an interview. The interviews indicated that both patients noted immediate improvement in the skin texture and a reduction in pain. This occurred within two days of initiating the treatment. The lesions were beginning to resolve by the one month interview. These individuals have been followed for 6 months and report continued improvement.

EXAMPLE 15

A 42 year female indoor soccer player who played goalie and suffered from repeated rug (indoor turf) burns on the knees was given a preparation of 1.0% wt/vol dermatan sulfate combined with 2.0% vol/vol wintergreen oil. This preparation was produced by adding 1.0 g of chondroitin sulfate B (obtained from SIGMA Chemical Company) to 100 mL of DI water and mixing until dissolved. To this solution was added the essential oil. This individual applied the solution immediately after the injury occurred and twice more at 4 hours and 12 hours after the injury. The patient commented that the solution caused great stinging and pain upon application. However, the rug burn was almost healed within 72 hours. This was compared to similar burns which she had sustained in past months which took up to 3 weeks to heal because they kept weeping. Since the patient was concerned about the stinging and pain upon application, a second formulation was prepared for her to try on the next rug burn. This second formulation contained the same chondroitin sulfate B mixed with 2.0% vol/vol Tea Tree Oil. Several weeks later the individual suffered another rug burn which was treated with the Tea Tree Oil preparation. The patient commented that this preparation was much better, causing only minimal discomfort upon application. The healing process again required only 96 hours instead of weeks. General comments were that the preparation caused the wound to produce a scab within a few hours and that this scab became dry and fell off within a few days. Additionally, the patient liked the fact that the solution was not greasy nor did it leave a lingering odor.

EXAMPLE 16

A formulation was prepared using Aloe Vera gel concentrate (a 99% pure gel obtained from Lily of the Desert) as a base, adding 0.2% wt/vol high molecular weight hyaluronic acid to it (obtained from LIPO Chemical Co., Inc. and found to contain >750,000 hyaluronic acid) and then adding 2.0% vol/vol Tea Tree Oil. This preparation was given to a veterinarian to use on a horse which suffered from recurrent problems with edema of the hock and stifle on the right rear leg. The solution was applied every 4 hours for 5 days. The veterinarian reported that by the end of this treatment the edema was gone and with one daily application after each exercise period, the edema had not returned (treatment continued 6 months). The veterinarian reported that he had never had a topical preparation which provided such good results.

EXAMPLE 17

A 45 year old female softball player tore the quadriceps muscles of both the right and left thighs. Within 4 hours of the injury, this individual was given a preparation containing 1.0% wt/vol high molecular weight (>750,000) hyaluronic acid (Genzyme, Inc.) mixed with 2.0% vol/vol Tea Tree Oil and 2.0% Wintergreen Oil (both oils obtained from Lorann Oils). The individual was also given FLEXALL 454 to use as a control. She used no ice or heat treatments after the injury. To the right quadriceps she applied the hyaluronic acid/Tea Tree Oil/Wintergreen Oil (preparation of this invention). To the left quadriceps she applied the FLEXALL 454 (Control). Three applications of each preparation were made during the late afternoon and evening on the day of the injury. By the time the first applications were made, this individual could not walk and both quadriceps were extremely painful. By the third application, the individual noted that the right quadriceps felt less painful. When the individual awoke the morning after the injury she immediately applied both preparations to the respective quadriceps and stayed in bed for one hour longer. After the one hour time period she decided to try to walk. The right quadriceps was reportedly much better and she was able to support weight on this leg (the quadriceps receiving the treatment of this invention). The left quadriceps was still as painful as it was the day before (no relief was noted). On the second day, 4 more applications of each preparation were made to the respective quadriceps. By the end of the day, the right quadriceps was "significantly improved" whereas the left quadriceps was more painful than the day before. On the morning of the third day post injury, after the morning application of the respective preparations, the individual reported that the right quadriceps felt "essentially normal" but the left quadriceps was still unchanged and very painful. At this time, the individual began using the treatment of this invention on the left quadriceps instead of the FLEXALL 454. Within 24 hours she reported that she could walk on the left leg and by 48 hours after switching treatments she was able to walk normally. In this direct comparison the hyaluronic acid/Tea Tree Oil/Wintergreen Oil formulation of this invention relieved the pain and inflammation of the muscle tear within 72 hours and, obviously stimulated healing, whereas an over-the-counter product suggested for this purpose was ineffective.

EXAMPLE 18

A 53 year old male burned his right forearm while working on the muffler of his motorcycle. The burned area was 8 cm×12 cm and was beginning to redden and raise at the time that a formulation of this invention was applied to the area. This individual had received a formulation prepared by combining 1.0% wt/vol high molecular weight hyaluronic acid (obtained from Lifecore Biomedicals, Inc. and demonstrating a molecular weight >500,000) with 1.0% chondroitin sulfate B (obtained from SIGMA) and adding 2.0% Rosemary Oil, approximately 8 months before this accident in order to treat a severe sunburn. He still had some of the formulation of this invention left and applied it immediately to the burn. He reported that it immediately felt cool and that within 5 minutes the severe pain had dissipated. The burn did not blister as he had expected. Within 24 hours all that was noticeable was a reddened area of skin which was not painful and not granulated. Within 5 days there was no indication that a burn had occurred.

EXAMPLE 19

A 52 year old male suffered a severe sunburn while boating. He tried several sunburn lotions to relieve the pain and redness but none of these preparations provided relief. He was feverish (temperature 101° F.). He was given a preparation containing 1.0% wt/vol high molecular weight hyaluronic acid (Lifecore Biomedical), 1.0% wt/vol low molecular weight hyaluronic acid (same preparation as described in EXAMPLE 1), 2.0% vol/vol Tea Tree Oil and 2.0% vol/vol Wintergreen Oil in an aqueous base. This was applied to his back, shoulders and arms. Within 5 minutes he commented that the burning sensation was gone. One hour after the application this patient's body temperature was back to normal. He continued to apply the preparation for 24 hours after which he discontinued treatment because he felt normal. The sunburned areas never peeled nor caused additional problems.

Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

What is claimed is:

1. A topical pharmaceutical composition which comprises as an active ingredient a pharmacologically effective amount of at least one low purity or cosmetic grade complex carbohydrate selected from the group consisting of oligosaccharides, sialylated oligosaccharides, polysaccharides and glycosaminoglycans, and at least one essential oil in an amount effective to allow penetration of the dermis of mammals by the complex carbohydrate.

2. The pharmaceutical composition according to claim 1, wherein said complex carbohydrate is a polysaccharide.

3. The pharmaceutical composition according to claim 1, wherein said complex carbohydrate is an oligosaccharide.

4. The pharmaceutical composition according to claim 1, wherein said essential oil is natural or synthetic.

5. The pharmaceutical composition according to claim 4, wherein said natural or synthetic essential oils are selected from the group consisting of Eucalyptus Oil, Rosemary Oil, Pine Needle Oil, Tea Tree Oil, Wintergreen Oil, Peppermint Oil, Spearmint Oil, Camphor Oil, Sage Oil, Jojoba Oil, Cinnamon Oil, Anise Oil, Lemon Oil, Lime Oil, Orange Oil, Clove Oil, Almond Oil, White Pine Oil, Cardamon Oil and Cedar Leaf oil.

6. The pharmaceutical composition according to claim 2, wherein said complex carbohydrate is selected from the group consisting of a glycosaminoglycan and a mannan.

7. The pharmaceutical composition according to claim 6, wherein said glycosaminoglycan is selected from the group consisting of hyaluronic acid, heparin, heparain sulfate, chondroitin sulfate, polysulfated glycosaminoglycan and keratan sulfate.

8. The pharmaceutical composition according to claim 1, wherein said complex carbohydrate is of low purity.

9. The pharmaceutical composition according to claim 2, wherein said complex carbohydrate is obtained from an extract of the Aloe Vera plant.

10. The pharmaceutical composition according to claim 3, wherein said complex carbohydrate is a sialylated oligosaccharide.

11. The pharmaceutical composition according to claim 4, wherein said essential oil is an aromatic oil.

12. The pharmaceutical composition according to claim 1, wherein said complex carbohydrate comprises a mixture of molecular weight ranges.

13. The pharmaceutical composition according to claim 12, wherein said complex carbohydrate comprises a mixture of a high molecular weight complex carbohydrate and a low molecular weight complex carbohydrate.

14. The pharmaceutical composition according to claim 13, wherein the high molecular weight and low molecular weight complex carbohydrate differ by molecular weight and chemical structure.

15. The pharmaceutical composition according to claim 13, wherein said high molecular weight and low molecular weight complex carbohydrates range from two different size polymers of the same complex carbohydrate.

16. The pharmaceutical composition according to claim 1, wherein said complex carbohydrate is in a concentration ranging from 0.1% to 99% wt/vol and said essential oil is in a concentration from 0.5% to 20% vol/vol.

17. The pharmaceutical composition according to claim 16, wherein said complex carbohydrate is in a concentration ranging from 0.5% to 3.0% wt/vol and said essential oil is in a concentration of between 0.5% and 3.0% vol/vol.

18. The pharmaceutical composition according to claim 1, wherein said complex carbohydrate is in a concentration ranging from 0.01% to 5.0% wt/vol and said essential oil is in a concentration ranging from 0.5% to 10% vol/vol in an Aloe Vera gel concentrate base with a concentration of between 50% and 99% vol/vol.

19. A pharmaceutical composition which comprises as an active ingredient a pharmacologically effective amount of at least one low purity or cosmetic grade complex carbohydrate selected from the group consisting of oligosaccharides, sialylated oligosaccharides, polysaccharides, and glycosaminoglycans and at least one essential oil in an amount effective to allow penetration of the dermis of mammals by the complex carbohydrate.

20. A topical pharmaceutical composition which consists essentially of as an active ingredient a pharmacologically effective amount of at least one complex carbohydrate selected from the group consisting of a mixture of high and low molecular weight ranges of low purity or cosmetic grade hyaluronic acid in a total concentration of between 0.5% and 3.0% wt/vol and at least one essential oil selected from the group consisting of Tea Tree Oil, Rosemary Oil, Peppermint Oil and Wintergreen Oil in a total concentration of between 0.5% and 3.0% vol/vol.

21. A method of treatment of inflammation, pain or itching which comprises topically applying to the skin of a mammal the composition of claim 19.

22. The method of claim 21, wherein said topical application is made directly over or on the site of inflammation, pain and itching.

23. The method of claim 21, wherein said inflammation, pain or itching results from arthritis, bursitis, athletic injuries, tendonitis, trauma, poor circulation, tired feet, allergies, poison ivy, insect bites/stings, sunburn, burns, edema related to diabetes, decubitus ulcers, dry skin or psoriasis.

24. The pharmaceutical composition of claim 19, wherein said complex carbohydrate is obtained from an extract of the Aloe Vera plant.

25. The pharmaceutical composition of claim 19, wherein said complex carbohydrate is in a concentration ranging from 0.1% to 99% wt/vol and said essential oil is in a concentration from 0.5% to 20% vol/vol.

26. The pharmaceutical composition of claim 19, wherein said complex carbohydrate is in a concentration ranging from 0.01% to 5.0% wt/vol and said essential oil is in a concentration ranging from 0.5% to 10% vol/vol in an Aloe Vera gel concentrate base with a concentration of between 50% and 99% vol/vol.

27. A method of inhibiting the inflammatory process by introducing a pharmacologically effective amount of at least one low purity or cosmetic grade complex carbohydrate selected from the group consisting of oligosaccharides, sialylated oligosaccharides, polysaccharides and glycosaminoglycans, which is biospecific for the adhesion cascade and blocks the binding of leucocytes to the epithelium during migration and extravasation of leucocytes to a site of trauma.

28. A method for inhibiting inflammation which comprises providing a pharmacologically effective amount of at least one low purity or cosmetic grade complex carbohydrate selected from the group consisting of oligosaccharides, sialylated oligosaccharides, polysaccharides and glycosaminoglycans, and which inhibits the adhesion cascade so as to inhibit binding of leucocytes to epithelium, mixing said compound with an essential oil to obtain a mixture, and applying said mixture to a site in need of treatment to inhibit inflammation.

29. The pharmaceutical composition according to claim 4, wherein said natural or synthetic essential oil is Menthol.

30. The method of claim 21, wherein said inflammation, pain or itching results from bruising, muscle cramping, superficial cuts and scrapes or open wounds.

31. The pharmaceutical composition according to claim 1, wherein said at least one complex carbohydrate has a molecular weight in the range of from 1,000 to less than 50,000 daltons.

32. The pharmaceutical composition according to claim 1, wherein said at least one complex carbohydrate has a molecular weight in the range of from 100,000 to 500,000 daltons.

33. The pharmaceutical composition according to claim 1, wherein said at least one complex carbohydrate has a molecular weight in the range of greater than 750,000 daltons.

34. The pharmaceutical composition according to claim 1, wherein the essential oil is present in a concentration of between 0.5% to 3% vol/vol.

35. A topical pharmaceutical composition consisting essentially of as an active ingredient a pharmacologically effective amount of at least one low purity or cosmetic grade complex carbohydrate selected from the group consisting of oligosaccharides, sialylated oligosaccharides, polysaccharides and glycosaminoglycans, and at least one essential oil in an amount effective to allow penetration of the dermis of mammals by the complex carbohydrate.

36. The pharmaceutical composition according to claim 1, which is in the form of an emulsion, suspension, solution, cream or ointment.

37. A composition for topically treating inflammation, pain or itching, comprising a pharmaceutically effective amount of a low purity or cosmetic grade glycosaminoglycan or mannan in combination with an essential oil present in an amount effective to allow penetration of the dermis of mammals by the glycosaminoglycan or mannan.

38. The composition according to claim 37, wherein the essential oil is selected from the group consisting of Tea Tree Oil, Rosemary Oil, Wintergreen Oil, Cinnamon Oil, Peppermint Oil, Spearmint Oil, Lemon Oil, Clove Oil, Cedar Leaf Oil and Orange Oil.

39. A method of treatment of inflammation, pain or itching which comprises topically applying to the skin of a mammal the pharmaceutical composition according to claim 6, wherein the essential oil is selected from the group consisting of Tea Tree Oil, Rosemary Oil, Wintergreen Oil, Cinnamon Oil, Peppermint Oil, Spearmint Oil, Camphor Oil, Clove Oil, and Cedar Leaf Oil.

40. The method of claim 39, wherein the inflammation, pain or itching results from arthritis, bursitis, athletic injuries, allergies, poison ivy, insect stings, sunburn, edema related to diabetes, decubitus ulcers, open wounds and psoriasis.

41. A method of treating pain and inflammation comprising topically applying a pharmaceutical composition consisting essentially of a low purity or cosmetic grade glycosaminoglycan or mannan combined with an essential oil present in an amount effective to allow penetration of the dermis of mammals by the glycosaminoglycan or mannan.

42. The method according to claim 41, wherein the glycosaminoglycan is selected from the group consisting of chondroitin sulfate, keratin sulfate, hyaluronic acid, dermatan sulfate and heparain sulfate and the essential oil is selected from the group consisting of Wintergreen Oil, Tea Tree Oil, Rosemary Oil, Clove Oil, Eucalyptus Oil, Camphor Oil, Peppermint Oil, Spearmint Oil and Cinnamon Oil.

43. The topical pharmaceutical composition of claim 1, wherein said composition is a pain-relieving composition.

44. The topical pharmaceutical composition of claim 19, wherein said composition is a pain-relieving composition.

45. The topical pharmaceutical composition of claim 20, wherein said composition is a pain-relieving composition.

46. The topical pharmaceutical composition of claim 35, wherein said composition is a pain-relieving composition.

47. The composition of claim 1, wherein the low purity or cosmetic grade complex carbohydrate contains up to 5% by wt. contaminants.

48. The composition of claim 1, wherein the low purity or cosmetic grade complex carbohydrate contains less than 98% by wt. hyaluronic acid.

49. A method of treatment of inflammation, pain or itching which comprises topically applying to the skin of a mammal the composition of claim 1.

50. The pharmaceutical composition of claim 1, wherein the active ingredient is present in an amount of at least 0.5% wt/vol.

51. The pharmaceutical composition of claim 1, wherein the active ingredient is present in an amount of at least 1% wt/vol.

52. The pharmaceutical composition of claim 1, wherein the essential oil is present in a concentration of between 0.5% to 20% vol/vol.

53. The pharmaceutical composition of claim 19, wherein the essential oil is present in a concentration of between 0.5% to 20% vol/vol.

54. The pharmaceutical composition of claim 28, wherein the essential oil is present in a concentration of between 0.5% to 20% vol/vol.

55. The pharmaceutical composition of claim 35, wherein the essential oil is present in a concentration of between 0.5% to 20% by vol/vol.

56. The pharmaceutical composition of claim 1, wherein the essential oil is present in a concentration of between 0.5% to 10% vol/vol.

57. The pharmaceutical composition of claim 1, wherein the essential oil is present in a concentration of between 1% to 3% vol/vol.

58. The topical pharmaceutical composition of claim 1, wherein the polysaccharides are selected from the group consisting of mannans and branched polysaccharides.

59. The topical pharmaceutical composition of claim 1, wherein said at least one low purity or cosmetic grade complex carbohydrate has a molecular weight in the range of from 1,000 to less than 50,000 daltons, from 100,000 to 500,000 daltons, or greater than 750,000 daltons.

60. The pharmaceutical composition of claim 19, wherein the polysaccharides are selected from the group consisting of mannans and branched polysaccharides.

61. The pharmaceutical composition of claim 19, wherein said at least one low purity or cosmetic grade complex carbohydrate has a molecular weight in the range of from 1,000 to less than 50,000 daltons, from 100,000 to 500,000 daltons, or greater than 750,000 daltons.

62. The method of claim 27, wherein the polysaccharides are selected from the group consisting of mannans and branched polysaccharides.

63. The method of claim 28, wherein the polysaccharides are selected from the group consisting of mannans and branched polysaccharides.

64. The topical pharmaceutical composition of claim 35, wherein the polysaccharides are selected from the group consisting of mannans and branched polysaccharides.

65. The topical pharmaceutical composition of claim 35, wherein said at least one low purity or cosmetic grade complex carbohydrate has a molecular weight in the range of from 1,000 to less than 50,000 daltons, from 100,000 to 500,000 daltons, or greater than 750,000 daltons.

* * * * *

UNITED STATES PATENT AND TRADEMARK OFFICE
CERTIFICATE OF CORRECTION

PATENT NO. : 5,888,984
DATED : March 30, 1999
INVENTOR(S) : Brown, et al

It is certified that error appears in the above-indentified patent and that said Letters Patent is hereby corrected as shown below:

On the title page: Item [75] Inventors: please add the second inventor's name as follows: -- Karen K. Brown --.

Signed and Sealed this

Seventeenth Day of April, 2001

*Attest:*

NICHOLAS P. GODICI

*Attesting Officer*  Acting Director of the United States Patent and Trademark Office